(12) United States Patent
He

(10) Patent No.: US 10,281,372 B2
(45) Date of Patent: May 7, 2019

(54) MULTI-CHANNEL HEADSPACE EXTRACTION NEEDLE

(71) Applicant: ChengDu Colin Analysis Technology Co., Ltd., Chengdu, Chengdu, Sichuan (CN)

(72) Inventor: Qifa He, Sichuan (CN)

(73) Assignee: CHENGDU COLIN ANALYSIS TECHNOLOGY CO., LTD., Sichuan (CN)

(*) Notice: Subject to any disclaimer, the term of this patent is extended or adjusted under 35 U.S.C. 154(b) by 155 days.

(21) Appl. No.: 15/538,163

(22) PCT Filed: Jun. 14, 2016

(86) PCT No.: PCT/CN2016/085695
§ 371 (c)(1),
(2) Date: Jun. 20, 2017

(87) PCT Pub. No.: WO2017/113625
PCT Pub. Date: Jul. 6, 2017

(65) Prior Publication Data
US 2018/0003596 A1    Jan. 4, 2018

(30) Foreign Application Priority Data

Dec. 28, 2015 (CN) .................... 2015 2 1097015 U

(51) Int. Cl.
*G01N 1/22* (2006.01)
*G01N 1/24* (2006.01)

(52) U.S. Cl.
CPC ............ *G01N 1/2226* (2013.01); *G01N 1/24* (2013.01); *G01N 2001/2229* (2013.01)

(58) Field of Classification Search
CPC . G01N 1/24; G01N 1/2226; G01N 2001/2229
See application file for complete search history.

(56) References Cited

U.S. PATENT DOCUMENTS

| 3,427,862 A * | 2/1969 | Hubner | ..................... G01N 1/24 73/23.2 |
| 4,336,722 A * | 6/1982 | Schweitzer | .............. G01N 1/24 73/863.12 |

(Continued)

FOREIGN PATENT DOCUMENTS

| CN | 202735140 U | 2/2013 |
| CN | 203164023 U | 8/2013 |

(Continued)

*Primary Examiner* — David J Bolduc
(74) *Attorney, Agent, or Firm* — Muncy, Geissler, Olds & Lowe, P.C.

(57) ABSTRACT

A multi-channel headspace extraction needle is provided. The extraction needle includes an inner needle tube, a sealed connector, and a needle rod and an outer needle tube respectively installed on a top portion and a bottom portion of the sealed connector. The sealed connector includes a first conduit and a second conduit connected with a tube lumen of the outer needle tube. A sealing layer is disposed between a bottom tube wall of the inner needle tube, which extends into the tube lumen of the outer needle tube, and a sidewall of the outer needle tube. The sidewall of the outer needle tube includes a first through-hole and a second through-hole respectively disposed above and under the sealing layer. The first through-hole is connected with the tube lumen of the outer needle tube and the second through-hole is connected with a tube lumen of the inner needle.

2 Claims, 5 Drawing Sheets

(56) References Cited

U.S. PATENT DOCUMENTS

| | | | | |
|---|---|---|---|---|
| 4,445,390 | A | * | 5/1984 | Atwell ................. G01N 33/203 73/863.21 |
| 5,496,741 | A | * | 3/1996 | Pawliszyn ............... G01N 1/405 436/163 |
| 5,844,148 | A | * | 12/1998 | Klein ................... G01N 1/2226 73/863.82 |
| 6,164,144 | A | * | 12/2000 | Berg ...................... G01N 1/405 73/863.21 |
| 7,674,631 | B2 | | 3/2010 | Pawliszyn |
| 8,205,512 | B1 | * | 6/2012 | Michalski ............ G01N 1/2211 73/863.41 |
| 2005/0014156 | A1 | * | 1/2005 | Pawliszyn ................ G01N 1/40 435/7.23 |
| 2012/0160038 | A1 | * | 6/2012 | Wells ....................... B01J 15/00 73/863.21 |
| 2013/0233054 | A1 | | 9/2013 | Oliphant et al. |
| 2014/0030818 | A1 | * | 1/2014 | Schueler ............. G01N 1/2214 436/178 |
| 2017/0059533 | A1 | * | 3/2017 | Ghiasvand ............. B01J 20/262 |
| 2018/0023448 | A1 | * | 1/2018 | Zhang .................... F01N 3/033 73/23.33 |
| 2018/0059009 | A1 | * | 3/2018 | Kagawa ................... G01N 1/38 |

FOREIGN PATENT DOCUMENTS

| | | |
|---|---|---|
| CN | 105606409 A | 5/2016 |
| CN | 205228898 U | 5/2016 |
| DE | 202010000391 U1 | 7/2010 |
| WO | 9115745 A1 | 10/1991 |

* cited by examiner

MULTI-CHANNEL HEADSPACE EXTRACTION NEEDLE

CROSS REFERENCE TO RELATED APPLICATIONS

This application claims the priority to PCT Application No. PCT/CN2016/085695, filed on Jun. 14, 2016, which claims the priority to Chinese Patent Application No. 201521097015.0, filed on Dec. 28, 2015 and entitled "MULTI-CHANNEL HEADSPACE EXTRACTION NEEDLE." The entire disclosures of the above application are incorporated herein by reference.

BACKGROUND OF THE INVENTION

Field of Invention

The present invention relates to an analysis technical field, and more particularly to a multi-channel headspace extraction needle.

Description of Prior Art

Headspace injection seals sample into headspace vial to volatilize the substance to be extracted into the upper space of the headspace vial by heating. Under certain conditions, the concentration of the volatile in the upper space of the vial maintains a balance with the concentration of the sample and the concentration of the sample can be tested and analyzed through the upper gas in the extraction vial. To extract and transfer the gas in the upper space of the headspace vial according to the analysis requirements to the gas chromatograph for analysis, the extraction needle is one of the important components in the entire extraction mechanism. The structure of the needle can determine the transferring way of the entire extraction mechanism.

Most extraction mechanism of the modern commercial headspace has single channel. The needle with pressurizes on the sample (adding the carrier gas) and extracts the sample by inserting the needle with single channel into the headspace vial. With the extraction of the sample gas, the pressure in the vial will reduce and the transfer of the headspace gas needs the help of external components. These components will not only absorb part of the sample but also spread the sample to all available space. This will cause loss and remain of the sample, minimum detectability too high and poor linearity. AutoHS auto headspace injector applies double flow needle to overcome the defects of pressure reducing in the headspace vial when injecting the sample and create an environment for extracting the sample directly. To further reduce the area of the sample contacted the components, the sample transfer is limited within the ideal straight pipe. But when pressurizing on the headspace vial, the pressure in the vial equals to the carrier gas pressure, the volatile substance can go into the carrier gas conduit by spreading reversely through the conduit as the prior headspace. The prior commercial headspace pressurizes when the needle inserts into the headspace vial, when the pressure in the vial equals to the carrier gas pressure, the volatile substance will go into the carrier gas conduit by spreading reversely and this will cause certain absorption and remain.

SUMMARY OF THE INVENTION

In order to overcome the technical problems, the present invention provides a multi-channel headspace extraction needle. It can reduce the remain sample in the headspace extraction system and ensure the integrity of sample extraction and front-end transmission to minimize the loss of the sample and keep the pressure steady.

The aim of the invention is to achieve by following operations.

The present invention provides a multi-channel headspace extraction needle, characterized in that the multi-channel headspace extraction needle comprises an inner needle tube, a sealed connector, and a needle rod and an outer needle tube respectively installed on a top portion and a bottom portion of the sealed connector, wherein the sealed connector comprises a first conduit and a second conduit connected with a tube lumen of the outer needle tube, wherein a sealing layer is disposed between a bottom tube wall of the inner needle tube, which extends into the tube lumen of the outer needle tube, and a sidewall of the outer needle tube, wherein a top end of the inner needle tube passes through a junction of the first conduit, the second conduit and the tube lumen of the outer needle tube to reach the top portion of the sealed connector to hermetically connecting with the sealed connector, and wherein the sidewall of the outer needle tube comprises a first through-hole and a second through-hole respectively disposed above and under the sealing layer, and wherein the first through-hole is connected with the tube lumen of the outer needle tube and the second through-hole is connected with a tube lumen of the inner needle.

In one embodiment, the first conduit and the second conduit are disposed on a same axis.

When applying the present invention, the position of the first conduit, the second conduit and the inner needle tube can be exchanged and the first conduit and the second conduit are installed on the sealed connector. The junction of the conduits lies in the nearest distance from the needle tip for needle to work, that is when the needle inserts into the headspace vial, it is in the nearest distance from the top of the constant temperature zone of the sample vial and the isolation layer on the constant temperature zone of the needle. The ends away from the needle assembly of the first conduit, the second conduit and the inner needle tube are connected with valves with different functions, the airflow direction and the airflow amount can be changed by the switch of the valves. When the carrier gas goes into the outer needle lumen through the first conduit or the second conduit and pressurize on the headspace vial, there will always be certain amount of the carrier gas entering from the first conduit and flowing out of the second conduit and the amount is controlled by the connected assembly so that the sample gas in the headspace vial cannot go into the first conduit, the second conduit, the input conduit of the carrier gas and the related carrier gas control system to avoid the remain of the sample gas contacting the carrier gas conduit and avoid taking the remain to the next sample when extracting the sample with pressure so avoid affecting the result accuracy. After the carrier gas pressurizing on the headspace vial, the pressure in the vial equals to the carrier gas and the inner needle tube controlled by the valve can connect directly with the sample transmission tube to transfer the sample to the gas chromatograph or other facilities for receiving the sample. The pressure in the vial will reduce in the transmission process while the second conduit or the first conduit will supplement the carrier gas to push the sample gas flow and keep the pressure in the vial steady. When the valve connected with the inner needle tube can ventilate, it can realize gas replacement. When work is done, the conduits of the needle will be cleaned by controlling the valve to change the direction of the airflow.

The multi-channel of the present invention is on the needle components but not on the connected conduit so reduce the contact area between the sample and the facility. The advantage of the present invention is to reduce the sample remain in the headspace extraction system to ensure the integrity of sample extraction and front-end transmission to minimize the loss of the sample and keep the pressure steady. It also the advantages of gas replacement and dynamic compensation injection.

Figure 1:
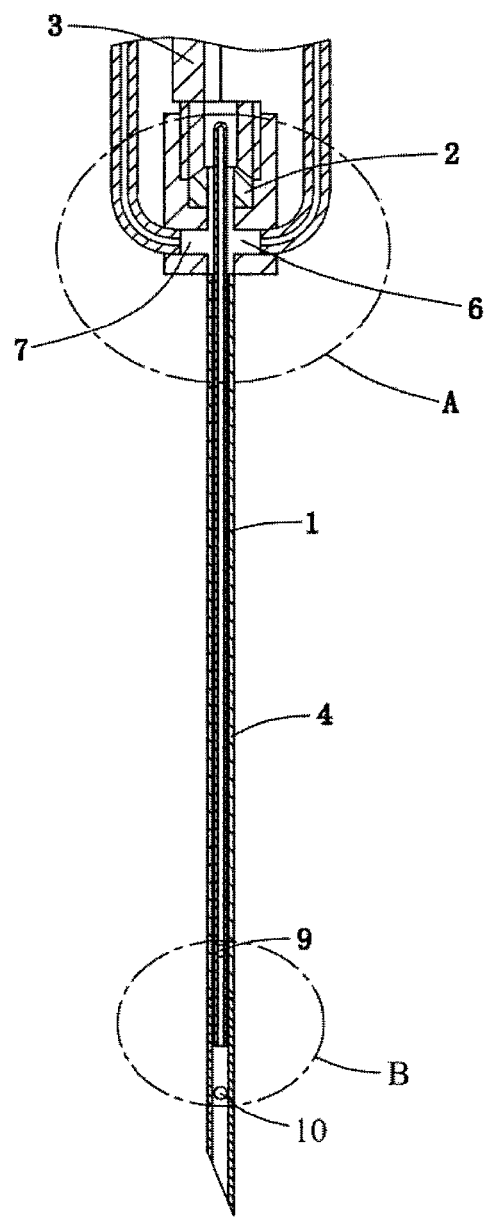
FIG. 1 is an illustrative view of the multi-channel headspace extraction needle according to one embodiment of the present invention.
Figure 2:
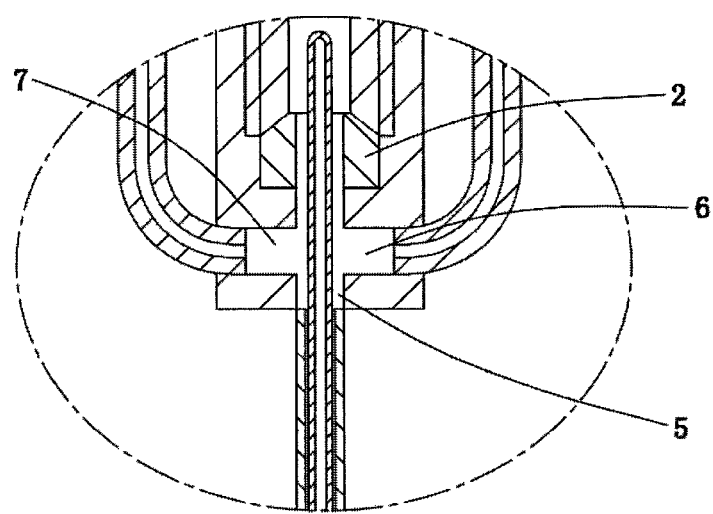
FIG. 2 is an enlarged illustrative view of region A of the FIG. 1 according to one embodiment of the present invention.
Figure 3:
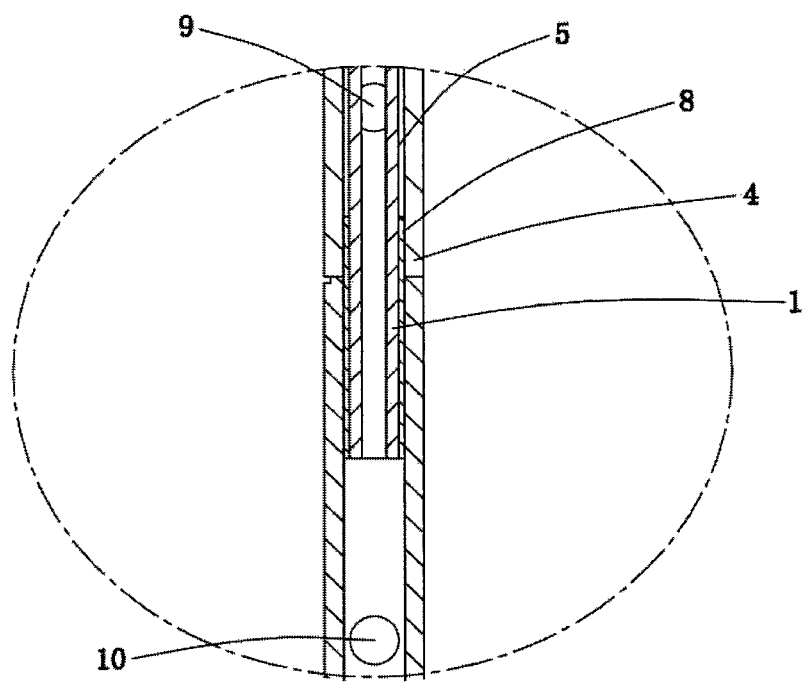
FIG. 3 is an enlarged illustrative view of region B of the FIG. 1 according to one embodiment of the present invention.
Figure 4:
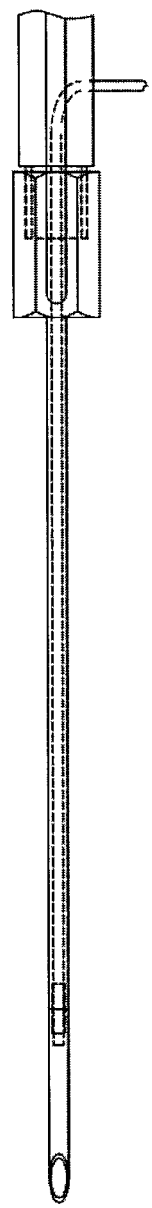
FIG. 4 is an illustrative left-side view of the FIG. 1 according to one embodiment.

REFERENCE NUMERALS inner needle tube 1;
sealed connector 2;
needle rod 3;
outer needle tube 4;
tube lumen of the outer needle tube 5;
first conduit 6;
second conduit 7;
sealing layer 8;
first through-hole 9;
second through-hole 10; and
headspace vial 11.

The following text will further describe the present invention with reference to the accompanying drawings. The embodiment is only to explain the present invention but not to limit the technical solution. Any person who skilled in the art may deform and modify the embodiment of the present invention within the spirit and scope of the appended claims, but these deformation and modification belong to the protection scope of the present invention.

DETAILED DESCRIPTION OF THE PREFERRED EMBODIMENTS

Please refer to FIG. 1 to FIG. 4. In one embodiment, a multi-channel headspace extraction needle includes an inner needle tube 1, a sealed connector 2, and a needle rod 3 and an outer needle tube 4 respectively installed on a top portion and a bottom portion of the sealed connector 2. A first conduit 6 and a second conduit 7 are disposed on a same axis. The sealed connector 2 includes the first conduit 6 and the second conduit 7 connected with a tube lumen of the outer needle tube 4. A sealing layer 8 is disposed between a bottom tube wall of the inner needle tube 1, which extends into the tube lumen of the outer needle tube 4, and a sidewall of the outer needle tube 4. A top end of the inner needle tube 1 passes through a junction of the first conduit 6, the second conduit 7 and the tube lumen of the outer needle tube 4 to reach the top portion of the sealed connector 2 to hermetically connecting with the sealed connector 2. The sidewall of the outer needle tube 4 includes a first through-hole 9 and a second through-hole 10 respectively disposed above and under the sealing layer 8. The first through-hole 9 is connected with the tube lumen of the outer needle tube 4 and the second through-hole 10 is connected with a tube lumen of the inner needle 1.

Figure 5:
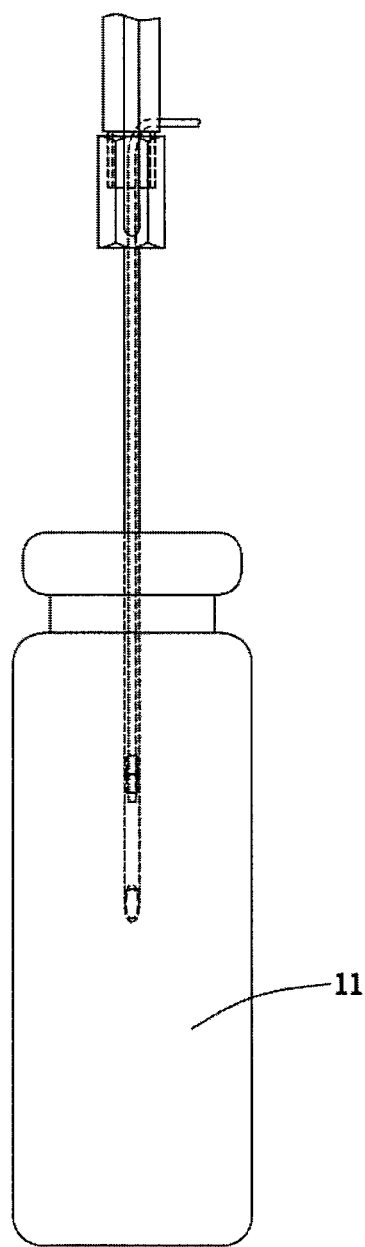
FIG. 5 is an illustrative view of pressurizing on the headspace vial according to one embodiment.

FIG. 5 is an illustrative view of pressurizing on the headspace vial 11 according to one embodiment.

As is understood by a person skilled in the art, the foregoing preferred embodiments of the present invention are illustrative rather than limiting of the present invention. It is intended that they cover various modifications and similar arrangements be included within the spirit and scope of the present invention, the scope of which should be accorded the broadest interpretation so as to encompass all such modifications and similar structures.

What is claimed is:

1. A multi-channel headspace extraction needle, comprising an inner needle tube, a sealed connector, and a needle rod and an outer needle tube respectively installed on a top portion and a bottom portion of the sealed connector, wherein the sealed connector comprises a first conduit and a second conduit connected with a tube lumen of the outer needle tube, wherein a sealing layer is disposed between a bottom tube wall of the inner needle tube, which extends into the tube lumen of the outer needle tube, and a sidewall of the outer needle tube, wherein a top end of the inner needle tube passes through a junction of the first conduit, the second conduit and the tube lumen of the outer needle tube to reach the top portion of the sealed connector to hermetically connecting with the sealed connector, and wherein the sidewall of the outer needle tube comprises a first through-hole and a second through-hole respectively disposed above and under the sealing layer, and wherein the first through-hole is connected with the tube lumen of the outer needle tube and the second through-hole is connected with a tube lumen of the inner needle.

2. The multi-channel headspace extraction needle according to claim 1, wherein the first conduit and the second conduit are disposed on a same axis.

* * * * *